United States Patent [19]

Pakulis

[11] Patent Number: 4,716,360

[45] Date of Patent: * Dec. 29, 1987

[54] MOISTURE DETECTOR APPARATUS AND METHOD

[75] Inventor: Ivars E. Pakulis, Arlington Heights, Ill.

[73] Assignee: Advanced Moisture Technology, Inc., Wauconda, Ill.

[*] Notice: The portion of the term of this patent subsequent to Nov. 27, 2001 has been disclaimed.

[21] Appl. No.: 766,426

[22] Filed: Aug. 16, 1985

[51] Int. Cl.$^4$ .................................. G01R 27/26
[52] U.S. Cl. ................................ 324/58.5 A; 343/753
[58] Field of Search ............. 219/10.55 F, 10.55 D, 219/10.55 R; 343/753; 324/58, 58.5

[56] References Cited

U.S. PATENT DOCUMENTS

| | | | |
|---|---|---|---|
| 2,659,860 | 11/1953 | Breazeale | 324/49 |
| 3,290,598 | 12/1966 | Thomas | 325/67 |
| 3,295,133 | 12/1966 | Emerson et al. | 343/18 |
| 3,460,030 | 8/1969 | Brunton et al. | 324/58.5 |
| 3,499,499 | 3/1970 | Bilbrough | 177/68 |
| 3,501,692 | 3/1970 | Kluck | 324/58.5 |
| 3,553,573 | 1/1971 | Lundstrom et al. | 324/58.5 |
| 3,634,756 | 1/1972 | Carlise | 324/58.5 A |
| 3,693,079 | 9/1972 | Walker | 324/58.5 A |
| 3,696,292 | 10/1972 | Busker | 324/58.5 A |
| 3,815,019 | 6/1974 | Wiles | 324/58.5 A |
| 3,818,333 | 6/1974 | Walker | 324/58.5 A |
| 3,833,906 | 9/1974 | Augustine | 343/753 |
| 3,851,244 | 11/1974 | Mounce | 324/58.5 A |
| 4,103,224 | 7/1978 | Taro et al. | 324/58.5 C |
| 4,104,584 | 8/1978 | Miyai et al. | 324/58.5 R |
| 4,131,845 | 12/1978 | Pakulis | 324/58.5 A |
| 4,206,399 | 6/1980 | Fitzky et al. | 324/58.5 C |
| 4,399,403 | 8/1983 | Strandberg | 324/58.5 A |
| 4,485,285 | 11/1984 | Pakulis | 324/58.5 A |

FOREIGN PATENT DOCUMENTS

| | | | |
|---|---|---|---|
| 0136657 | 7/1979 | Fed. Rep. of Germany | 324/58.5 A |
| 0016745 | 2/1979 | Japan | 219/10.55 F |
| 0022403 | 2/1984 | Japan | 343/753 |
| 0293208 | 12/1971 | U.S.S.R. | 324/58.5 A |

OTHER PUBLICATIONS

Du: "Microwave Lens Design . . . "—Microwave Journal, Sep. 1976-pp. 49–52.
"An Improved Microwave Method of Moisture Content Measurement and Control", by Kraszewski & Kulinski, IEEE Transactions on Industrial Electronics and Control Instrumentation, vol. IECI-23, No. 4, pp. 364–370, published by Institute of Electrical and Electronic Engineers, Nov. 1976.
"Microwave Antenna Theory and Design", Rad. Lab. Series, vol. 12, Sec. 11–3, S. Silver.

Primary Examiner—Reinhard J. Eisenzopf
Assistant Examiner—Jose M. Solis
Attorney, Agent, or Firm—Wood, Dalton, Phillips, Mason & Rowe

[57] ABSTRACT

An apparatus and method for providing improved measurement of moisture in a sample cell by use of microwave energy. Improved accuracy and reliability of the moisture determination is obtained by causing solely parallel beam, planar wavefront microwave energy to be passed through the sample in the test cell. The apparatus includes transmitting and receiving antennas and refractor elements (lenses) interposed between the antennas and the sample cell. The antennas, refractor elements, and sample cell may be located within an anechoic chamber. The invention comprehends locating the sample cell in the near field of the transmitting antenna and coordinating the characteristics of the refractor elements with the spacing of the antennas relative to the sample cell.

28 Claims, 3 Drawing Figures

MOISTURE DETECTOR APPARATUS AND METHOD

TECHNICAL FIELD

This invention relates to moisture measuring apparatuses and more specifically to a method and apparatuses utilizing microwave energy in measuring the relative moisture in a material sample.

BACKGROUND ART

In my recently issued U.S. Pat. No. 4,485,284, an apparatus and process is disclosed for enabling the measurement of moisture in a sample cell by use of microwave energy. As shown therein, the microwave energy is transmitted from a transmitting antenna, passed through the sample cell containing the material of which the moisture content is to be determined, and to a receiving antenna.

In this and similar devices, the microwave antenna for transmission and reception of the microwave energy generates a divergent beam with a spherical wavefront. The materials to be measured by the microwave signal means are in relatively close proximity to the microwave antennas in what is commonly referred to in the art as the "near field" of an antenna. The dielectric properties of materials in the near field of an antenna are known to influence the antenna beam pattern.

The dielectric properties of water are significantly different from most other materials. Thus, changes in moisture content significantly alter the dielectric properties of the materials to be measured. However, this also results in an altered antenna beam pattern in such moisture detectors using microwave signal means. In measuring homogeneous materials where the moisture is uniformly distributed within the sample material, the changes in antenna pattern due to moisture changes become part of the calibration with no detrimental effects in most cases. Inhomogeneous materials containing varying densities, lumps, air voids, or nonuniform distribution of moisture within the sample are much more difficult to measure using a conventional microwave beam. The effect of material nonuniformities and resultant discontinuities in the antenna pattern due to nonuniform dielectric properties create inaccuracies in measurement. The magnitude of the discontinuity effect due to nonuniform dielectric properties depends on where the discontinuity is located within the microwave beam pattern and the angle of incidence of the divergent microwave beam and the discontinuity.

DISCLOSURE OF INVENTION

The present invention comprehends an improved apparatus and method for microwave moisture analysis including means for causing solely parallel beam, planar wavefront microwave energy to be passed through the sample cell means for use by the moisture determining means in determining the moisture content of the sample.

In the illustrated embodiment, the means for causing solely parallel beam, planar wavefront microwave energy to be passed through the sample means includes means for forming a chamber effectively preventing reflection of the microwave energy adjacent the sample cell means.

In the illustrated embodiment, the means for causing solely parallel beam, planar wavefront microwave energy to be passed through the sample cell means includes means for generating microwave energy in the form of a divergent beam having a spherical wavefront and means for converting the beam to a parallel beam having a plane wavefront to be passed through the sample cell means.

The invention comprehends the provision of refractor means for effecting the refraction of the divergent beam to the parallel beam configuration.

The invention further comprehends the provision of refractor means for collecting the microwave energy passed through the sample means.

In the illustrated embodiment, the refractor means defines a hyperbolic surface facing away from the sample cell means and a planar surface facing the sample cell means.

In the illustrated embodiment, each of the antennas, the refractor means, and the sample cell means is enclosed within the anechoic chamber means.

Thus, the invention comprehends an improved structural arrangement wherein the microwave energy is caused to pass through the material in the sample cell means in the form of a parallel beam having a planar wavefront, with distortion of the desired microwave energy beam by extraneous reflected energy being effectively precluded by the disposition of the structure within an anechoic chamber defined by wall means preventing reflection of microwave energy which may impinge thereon. It has been found that the apparatus of the present structure provides a substantial improvement in the accuracy and facility of moisture determination in such apparatus.

Converting the divergent microwave beam into a parallel beam planar wavefront eliminates the varying angle of incidence effect arising in the prior art devices and provides improved precision of moisture measurement in nonuniform materials.

The invention is extremely simple and economical of construction while yet providing the highly desirable improvement and features discussed above.

BRIEF DESCRIPTION OF THE DRAWING

Other features and advantages of the invention will be apparent from the following description taken in connection with the accompanying drawing wherein.

BEST MODE FOR CARRYING OUT THE INVENTION

Figure 1:
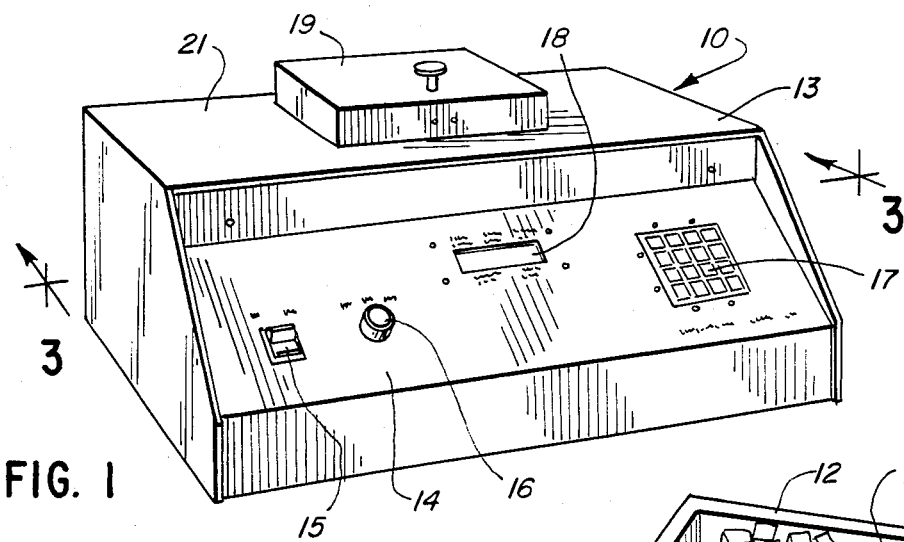
FIG. 1 is a perspective view of an apparatus for use in microwave moisture analysis embodying the invention.
Figure 2:
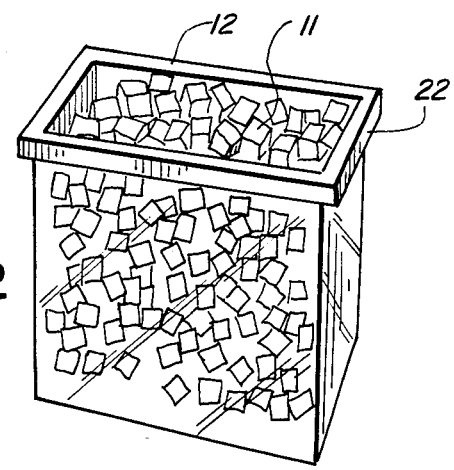
FIG. 2 is a perspective view of a sample cell containing material to be analyzed in the apparatus of the invention.

In the illustrative embodiment of the invention as disclosed in the drawing, an apparatus generally designated 10 is provided for analyzing the moisture content of a sample material 11 provided in a sample cell receptacle 12.

Figure 3:
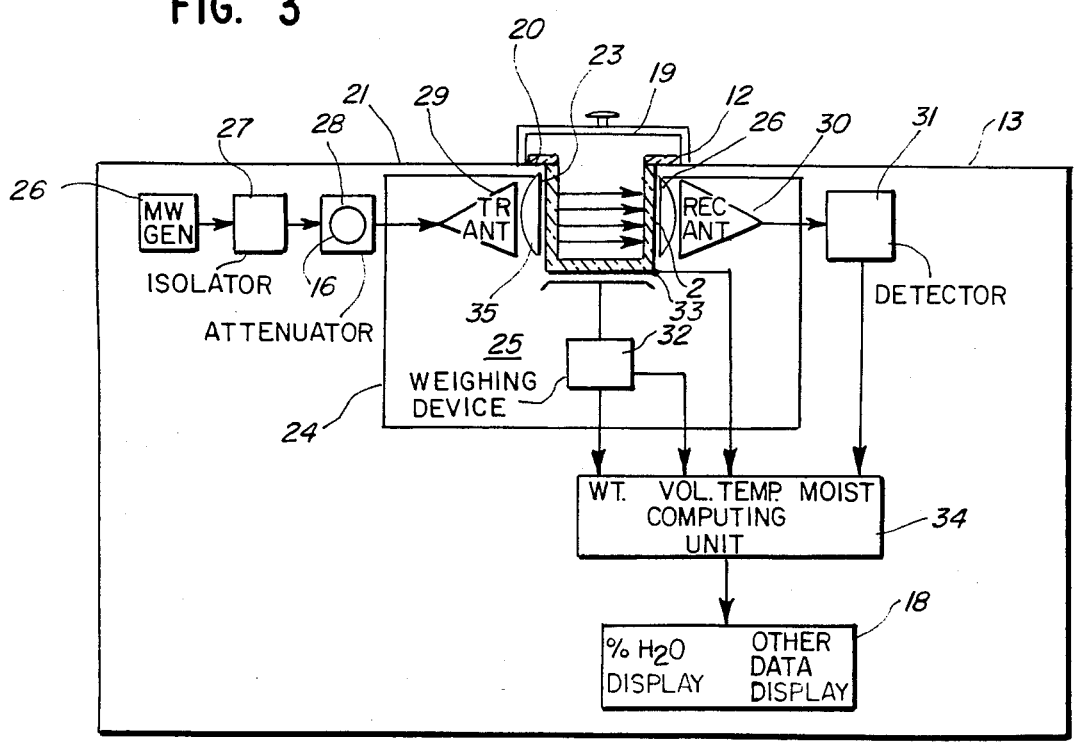
FIG. 3 is a schematic diagram of the microwave moisture measuring apparatus of the present invention.

As seen in FIG. 1, the apparatus is provided in a cabinet 13 defining a control panel surface 14, having an on-off switch 15, range control knob 16, input keyboard 17, and a readout display element 18 for indicating information concerning the moisture analysis. A removable cover 19 is provided for removably overlying an opening 20 provided in an upper wall portion 21 of the cabinet 13 through which the sample cell 12 is installed in the apparatus As shown in FIG. 3, the sample cell 12 is received within the cabinet 13, being supported by an upper peripheral flange 22 thereof on the upper wall 21 of the cabinet surrounding opening 20 for automatic disposition of the sample material in a test position within the cabinet. As further shown in FIG. 3, the sample cells extends downwardly through an opening 23 in an enclosure 24 defining an anechoic wall means preventing reflection of microwave energy impinging thereon. The anechoic chamber 25 defined by the wall means 24 is thusly free of reflected or re-emitted microwave energy.

Referring further to the structure illustrated in FIG. 3, the microwave energy passed through the cell 12 is generated in a conventional microwave generator 26 illustratively providing 10 to 100 milliwatts of microwave energy. The microwave energy developed by generator 26 is passed through an isolator 27 which prevents microwave reflection from traveling back to the generator.

After passing through the isolator, the microwave energy is passed through a level set attenuator 28 which is adjustably set by the control knob 16. The microwave energy is delivered from the attenuator to a transmitting antenna 29, which may comprise a conventional horn antenna, defining a point source of microwave radiation. The construction of the generator 26, isolator 27, attenuator 28, and transmitting antenna 29 is conventional and well known to those skilled in the art.

In the illustrated embodiment, the generator provides the microwave energy at 10.525 GHz, it being understood that any suitable frequency may be employed within the conventional range of approximately 2 GHz to 25 GHz.

The receiving antenna 30 receives the microwave energy after it is passed through the cell 12 and the sample material 11 contained therein. The receiving antenna may similarly comprise a conventional microwave horn antenna and is connected to a detector 31 which rectifies the microwave energy to provide it with an output signal.

As disclosed in my above-identified U.S. Pat. No. 4,485,284, the apparatus may further include a weighing device 32, a temperature sensor 33, and a computing unit 34 for receiving signals from the weighing device, the temperature sensor 33 and the detector 31.

The output of the computing unit 34 is provided to the display 18 for providing the user of the apparatus the desired information as to moisture content and other parameters of the sample. The display 18 may comprise a conventional readout display well known to those in the art. Thus, as indicated in FIG. 3, the display 18 may display, in digital form, the percentage of water in the sample, as well as other data, such as the date, time, product number, and density.

The computing unit 34 comprises a conventional digital computer having analog inputs which may be changed to digital outputs by the computer. The computer calculates the percent moisture and bulk density from the appropriate input information.

The invention comprehends the inclusion in the apparatus 10 of means for causing the microwave energy passed through the sample cell 12 to be solely parallel beam, planar wavefront microwave energy. It has been unexpectedly found that the utilization of such a microwave energy beam configuration provides a substantially improved moisture sensing operation, providing greater accuracy and facilitated testing.

More specifically, the invention comprehends the provision of a refractor 35 interposed between the transmitting antenna 29 and one side of the test cell 12. The refractor, as seen in FIG. 3, is defined by a hyperbolic convex surface facing away from the sample cell 12, and a planar surface facing toward the cell. The refractor converts the divergent microwave energy beam having a spherical wavefront delivered from the horn antenna 29 to a parallel beam having a plane wavefront before transmitting the microwave energy through the test cell 12. The use of the anechoic chamber 25 effectively maintains the desired parallel beam configuration of the microwave energy and cooperates with the refractor in providing the improved functioning of the apparatus.

As further illustrated in FIG. 3, a second refractor 36 may be interposed between the opposite side of the test cell and the receiving antenna 30. Refractor 36 is defined by a planar surface facing the test cell and a hyperbolic convex surface facing away from the test cell toward the receiving antenna 30.

The transmitting antenna 29 defines a near field in which the test cell 12 is disposed. It has been found that the refractor effectively prevents spurious sensing as by changes in the material density and uniformity, notwithstanding the provision of the test material in the near field of the transmitting antenna. Conventionally, such changes affect the antenna characteristics so as to cause spurious response of the apparatus to properties of the test material other than the moisture content thereof, thereby reducing the accuracy of the moisture determination. The use of the refractor 35 effectively precludes such adverse effect on the accuracy of the readout, thereby providing an improved facilitated determination of the moisture content of the test sample.

It has been found that the use of the parallel beam microwave energy substantially eliminates the varying angle of incidence effect and reduces undesired interaction between the material and the antenna field characteristics so as to provide such highly desirable improved accuracy in the sensing operation.

Thus, broadly, the invention comprehends the conversion of a spherical wavefront antenna radiation to a plane wavefront radiation for improved moisture determination in a moisture analysis apparatus. The invention comprehends the use of refracting means to convert a horn antenna pattern to a radiation having a plane wavefront in the near field of the horn antenna for use in measuring moisture content of material samples.

The invention further comprehends the use of refracting means for collecting the transmitted microwave energy and delivering it to the receiving horn antenna. It has been found that the use of the refracting means provides for a substantially improved moisture measurement in a novel and simple manner.

The foregoing disclosure of specific embodiments is illustrative of the broad inventive concepts comprehended by the invention.

I claim:

1. An apparatus for analyzing a sample of moisture containing material comprising:
    first means for forming a chamber effectively preventing reflection of microwave energy;
    second means defining a sample cell space for retaining a moisture containing sample material, said second means being arranged to be disposed in said chamber;

third means for transmitting microwave energy in the form of a parallel beam, planar wavefront through said second means in said chamber;

fourth means for receiving radiation transmitted through said space and providing a first output signal representative of water weight in a sample material therein;

fifth means coupled to said first and second means for providing a second output signal representing the weight of a sample material including the water weight retained in said space;

sixth means for receiving said first and second output signals and providing a third output signal representing the percent by weight moisture content of material retained in said space; and seventh means for measuring the temperature of the sample material retained in said space during a weight sensing operation and providing a fourth output signal.

2. An apparatus for analyzing a sample of moisture containing material comprising:

a source of microwave energy of predetermined frequencies;

transmitter means coupled to said source for transmitting said microwave energy in the form of a parallel beam, plane wavefront;

wall means forming a chamber effectively preventing reflection of microwave energy;

sample cell means removably positioned in said chamber in the path of said transmitted microwave energy for retaining a sample of moisture containing material in the path of said microwave energy such that said transmitted microwave energy is attenuated by moisture in said sample in said path, said sample cell means being substantially transparent to microwave energy at said predetermined frequencies;

receiver means positioned to receive microwave energy transmitted through said chamber by said transmitter means and providing an output representing the microwave energy transmitted through said sample cell means;

means coupled to said receiver means for providing a signal corresponding to the output signal representing the weight of the sample material retained therein;

temperature sensing means coupled to said sample cell means for detecting the temperature of the sample material retained in said sample cell means during the transmission of microwave energy therethrough;

output means coupled to simultaneously receive said output signals representing water weight, sample weight and sample material temperature for calculating and providing an output signal representing percent by weight moisture of a sample material; and anechoic chamber means enclosing each of said transmitter means, receiver means and sample cell means within a chamber constructed and designed to absorb microwave radiation at said predetermined frequencies to reduce microwave reflections and emissions within said chamber.

3. The apparatus of claim 1 wherein said third means comprises means for causing solely parallel beam, planar wavefront microwave energy to be passed through said sample cell means.

4. The apparatus of claim 2 wherein said transmitter means comprises means for causing solely parallel beam, planar wavefront microwave energy to be passed through said sample cell means.

5. The apparatus of claim 3 wherein said third means includes means for generating microwave energy in the form of a divergent beam having a spherical wavefront, and means for converting said beam to a parallel beam having a plane wavefront to be passed through the sample cell means.

6. The apparatus of claim 5 wherein said means for generating microwave energy comprises a horn antenna.

7. The apparatus of claim 5 wherein said microwave energy defines a near field and said sample cell means is disposed in said near field.

8. The apparatus of claim 3 wherein said means for causing solely parallel, planar wavefront microwave energy to be passed through said sample cell means includes refractor means.

9. The apparatus of claim 8 wherein said refractor means defines a hyperbolic convex surface facing away from said sample cell means.

10. The apparatus of claim 8 wherein said refractor means defines a hyperbolic convex surface facing away from said sample cell means and a plane surface facing said sample cell means.

11. The apparatus of claim 3 wherein said fourth means includes refractor means for collecting microwave energy transmitted through said sample cell means.

12. The apparatus of claim 11 wherein said refractor means defines a hyperbolic convex surface facing away from said sample cell means.

13. The apparatus of claim 3 wherein said means for causing solely parallel, planar wavefront microwave energy to be passed through said sample cell means includes a first refractor means for converting said beam to a parallel beam having a plane wavefront to be passed through the sample cell means, and a second refractor means for collecting microwave energy transmitted through said sample cell means.

14. The apparatus of claim 13 wherein each of said refractor means defines a hyperbolic convex surface facing away from said sample cell means.

15. The apparatus of claim 13 wherein each of said refractor means defines a hyperbolic convex surface facing away from said sample cell means and a plane surface facing said sample cell means.

16. The apparatus of claim 3 wherein said means for causing solely parallel, planar wavefront microwave energy to be passed through said sample cell means includes means for generating microwave energy in the form of a beam diverging from a substantially point source and having a spherical wavefront, and means for converting said beam to a parallel beam having a plane wavefront to be passed through the sample cell means.

17. The apparatus of claim 4 wherein said receiver means includes refractor means for collecting microwave energy transmitted through said sample cell means.

18. The apparatus of claim 17 wherein said refractor means defines a hyperbolic convex surface facing away from said sample cell means.

19. The apparatus of claim 4 wherein said transmitter means includes a first means for converting said beam to a parallel beam having a plane wavefront to be passed through the sample cell means, and a second refractor means for collecting microwave energy transmitted through said sample cell means.

20. The apparatus of claim 19 wherein each of said refractor means defines a hyperbolic convex surface facing away from said sample cell means.

21. The apparatus of claim 19 wherein each of said refractor means defines a hyperbolic convex surface facing away from said sample cell means and a plane surface facing said sample cell means.

22. The apparatus of claim 4 wherein said transmitter includes means for generating microwave energy in the form of a beam diverging from a substantially point source and having a spherical wavefront, and means for converting said beam to a parallel beam having a plane wavefront to be passed through the sample cell means.

23. The apparatus of claim 4 wherein said transmitter means includes means for generating microwave energy in the form of a divergent beam having a spherical wavefront, and means for converting said beam to a parallel beam having a plane wavefront to be passed through the sample cell means.

24. The apparatus of claim 23 wherein said means for generating microwave energy comprises a horn antenna.

25. The apparatus of claim 23 wherein said microwave energy defines a near field and said sample cell means is disposed in said near field.

26. The apparatus of claim 4 wherein said means for causing solely parallel, planar wavefront microwave energy to be passed through said sample cell means includes refractor means.

27. The apparatus of claim 26 wherein said refractor means defines a hyperbolic convex surface facing away from said sample cell means.

28. The apparatus of claim 26 wherein said refractor means defines a hyperbolic convex surface facing away from said sample cell means and a plane surface facing said sample cell means.

* * * * *